United States Patent [19]

Flohe et al.

[11] Patent Number: 4,788,179

[45] Date of Patent: Nov. 29, 1988

[54] METHOD OF TREATING AMYOTROPHIC LATERAL SCLEROSIS WITH DIPEPTIDE DERIVATIVES AND PHARMACEUTICAL COMPOSITIONS FOR USE THEREIN

[75] Inventors: Leopold Flohe, Roetgen; Hans Barth, Aachen, both of Fed. Rep. of Germany

[73] Assignee: Gruenenthal GmbH, Stolberg, Fed. Rep. of Germany

[21] Appl. No.: 807,845

[22] Filed: Dec. 11, 1985

[30] Foreign Application Priority Data

Dec. 18, 1984 [DE] Fed. Rep. of Germany ....... 3446127
Dec. 22, 1984 [DE] Fed. Rep. of Germany ....... 3447260

[51] Int. Cl.$^4$ ............................................. A61K 37/02
[52] U.S. Cl. ...................................................... 514/19
[58] Field of Search ........................................... 514/19

[56] References Cited

U.S. PATENT DOCUMENTS

| 4,045,556 | 8/1977 | Schwertner et al. | 514/19 |
| 4,386,073 | 5/1983 | Kisfaludy et al. | 514/18 |
| 4,608,365 | 8/1986 | Engel | 514/18 |

FOREIGN PATENT DOCUMENTS 1564078  4/1980  United Kingdom .

OTHER PUBLICATIONS

Engel et al., "Effect on Weakness and Spasticity in Amyotrophic Lateral Sclerosis of Thyrotropin-Releasing Hormone", *Lancet*, 7/09/83, pp. 73–75.
Engel et al., "Further Clinical Studies of TRH in ALS and Other Motor Neuron Disorders", *Neurology*, vol. 34 (Suppl. 1), p. 238.
Munsat et al., "Intrathecal TRH in Amyotrophic Lateral Sclerosis: Preliminary Observations", *Neurology*, vol. 34 (Suppl. 1), p. 239.
Mitsuma et al., "Concentrations of Immunoreactive Thyrotropin-Releasing Hormone in Spinal Cord of Patients . . . ", *Amer. J. Med. Sci.*, vol. 287, No. 2, pp. 34–36.
Schmidt-Achert et al., "Thyrotropin-Releasing Hormone Enhances Choline Acetyltransferase and Creatine Kinase . . . ", *J. Neurochemistry*, vol. 43, No. 2, pp. 586–589.
Imoto et al., "Amyotrophic Lateral Sclerosis: A Double-Blind Crossover Trial of Thyrotropin-Releasing Hormone", *J. Neurology, Neurosurgery*, vol. 47, pp. 1332–1334.
Braun et al., "Pulmonary Effects of Thyrotropin-Releasing Hormone in Amyotrophic Lateral Sclerosis", *Lancet*, 9/01/84, pp. 529–530.
Thielen et al., "Versuchsweiser Einsatz von TRH und TRH-Analogon bei Amyotropher Lateralsklerose", *Psycho*, No. 11 (1985), pp. 380–383.
Stober et al., "Intrathecal Thyrotropin-Releasing Hormone Therapy of Amyotrophic Lateral Sclerosis", *J. Neurol.*, 232: 13–14 (1985).
Jerusalem et al., *J. Neurol.*, 232 (Suppl.), 35 (1985).
Green et al., "Behavioural Effects of Central and Peripheral Injection of Two Synthetic Analogues of TRH", *Pro. of the B.P.S.*, Apr. 9–11, 1980, pp. 81P–82P.
Griffiths et al., "Locomotor Stimulant Actions of Some TRH Analogues", *Pro. of the B.P.S.*, Sep. 16–18, 1981, pp. 868P–869P.
Sobue et al., "Effect of Thyrotropin-Releasing Hormone on Ataxia of Spinocerebellar Degeneration", *Lancet*, Feb. 23, 1980, pp. 418–419.
Yehuda et al., "Effects of TRH and PS-24 on Colonic Temperature and Motor Activity of Rats: Possible Role Dopamine", *Peptides*, vol. 2, pp. 131–135 (1981).

*Primary Examiner*—J. R. Brown
*Assistant Examiner*—F. T. Moezie
*Attorney, Agent, or Firm*—Foley & Lardner, Schwartz, Jeffery, Schwaab, Mack, Blumenthal & Evans

[57] ABSTRACT

A method of treating patients suffering from amyotrophic lateral sclerosis (ALS) by administering dipeptide derivatives of the formula

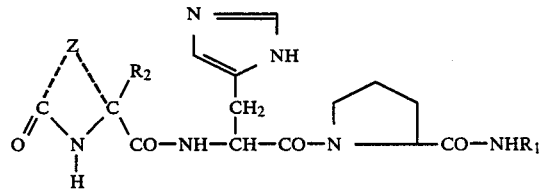

wherein $R_1$ is hydrogen, a lower alkyl group, cyclohexyl or benzyl; Z is one of the groups

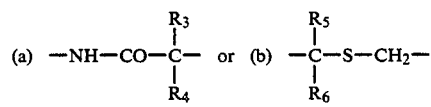

wherein if Z is a group (a), $R_2$ and $R_3$ together represent an additional bond between the carbon atoms bearing $R_2$ and $R_3$, or if Z is a group (b), $R_2$ is hydrogen; $R_4$ and $R_5$ are hydrogen or lower alkyl, or $R_5$ may also be phenyl; and $R_6$ is hydrogen or methyl; hydrates or pharmaceutically acceptable acid additions salts thereof. Pharmaceutical compositions containing effective ALS symptom counteracting amounts of such dipeptide derivatives may be administered by infusion, injection, orally, rectally or percutaneously.

10 Claims, No Drawings

METHOD OF TREATING AMYOTROPHIC LATERAL SCLEROSIS WITH DIPEPTIDE DERIVATIVES AND PHARMACEUTICAL COMPOSITIONS FOR USE THEREIN

BACKGROUND OF THE INVENTION

Amyotrophic lateral sclerosis (hereinafter abbreviated as "ALS") is a relentlessly progressive disease of the nervous system in the course of which the motor nerves, which carry orders for each body movement from the brain to the muscles, are destroyed. Lacking these instructions, the muscles waste away. Walking, speaking and finally breathing become impossible. Throughout the degeneration process, the victim's intellect remains clear, i.e. healthy, active minds find themselves trapped in increasingly useless, dying bodies. Death follows within an average of five years from the onset of symptoms. The cause of this disease is unknown, and up to now it has been impossible to cure ALS or to achieve clinical benefit for more than a few days.

It now surprisingly has been found that administration of dipeptide derivatives of the formula

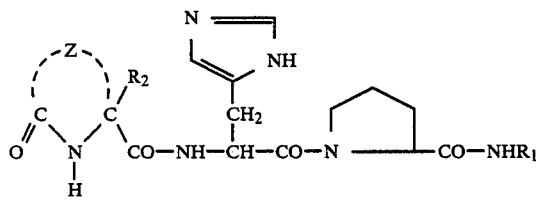

wherein $R_1$ represents a hydrogen atom, an alkyl group containing one to six carbon atoms, a cyclohexyl group or a benzyl group, Z is one of the following groups (attached to the CO-group in the ring by the valence marked with an asterisk)

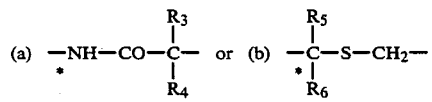

wherein if Z represents the group (a), $R_2$ and $R_3$ together represent an additional bond between the carbon atoms to which $R_2$ and $R_3$ are attached, or if Z represents the group (b), $R_2$ is a hydrogen atom, $R_4$ and $R_5$ may be the same or different and each represents hydrogen or an alkyl group containing one to three carbon atoms and wherein $R_5$ also may represent a phenyl group, and $R_6$ represents a hydrogen atom or a methyl group in anhydrous or hydrated forms and pharmaceutically acceptable salts of these compounds with acids preferably in form of suitable pharmaceutical compositions can cause remarkable improvements in the clinical symptoms of ALS patients lasting for up to several weeks after medication ended.

The compounds of formula I (and hydrates and acid addition salts thereof) and their preparation have been described, e.g., by Schwertner et al in "Structure and Activity of Natural Peptides" (Editors W. Voelter and G. Weitzel) Walter de Gruyter-Verlag, Berlin—New York 1981, pp. 397–415, in U.S. Pat. No. 4,045,556 and British Pat. No. 1,564,078, and elsewhere. The disclosures of these documents are hereby incorporated herein by reference.

In the cited publications it has been found that the compounds of formula I on parenteral or oral administration provide long-lasting central nervous system stimulating effects and that the toxicity of the compounds is very low. Due to these pharmacological properties the compounds of formula I according to the publications mentioned above and further references can be used as psycho-stimulating agents or as anti-depressive agents.

The prior known fields of use for the compounds of formula I accordingly was limited to diseases in which the brain falls ill causing disturbances of the intellect or mind, without (obligatory) influence on or degeneration of the motor nerves. As explained above, in ALS patients quite to the contrary the motor nerves become destroyed, but the intellect remains clear and the minds remain healthy and active. Therefore it was unforeseeable that the compounds of formula I or medicaments containing them, respectively, may cause improvements in the condition of ALS patients showing completely different symptoms in comparison to those shown by patients suffering from psychiatric disorders.

SUMMARY OF THE INVENTION

It is the object of the present invention to provide a method of treating patients suffering from amyotrophic lateral sclerosis with dipeptide derivatives of the formula I, hydrates or pharmaceutically acceptable acid addition salts thereof.

Another object of the invention is to provide pharmaceutical compositions containing dipeptide derivatives of the formula I and hydrates or pharmaceutically acceptable salts of these compounds with acids (such salts herein also are called "acid addition salts") for use in the aforementioned method of treating patients suffering from amyotrophic lateral sclerosis.

These and other objects of the invention are achieved by administering to a patient suffering from amytrophic lateral sclerosis a therapeutically effective ALS symptom counteracting amount of a compound of formula I.

The manner in which the compound of formula I is administered as well as the amount of this compound which is therapeutically effective in the specific patient to be treated depend on the state of the disease in the individual patient at the beginning of the treatment and can be individually determined by the attending physician in each case.

The compounds of formula I as well as their hydrates and salts are relatively stable products. Thus no problems or difficulties are encountered by a skilled pharmacist in their incorporation into pharmaceutical compositions in the form and amount desired by the physician.

DETAILED DESCRIPTION OF PREFERRED EMBODIMENTS

In general all compounds of formula I, their hydrates and their pharmaceutically acceptable salts with acids are suitable for use to treat patients suffering from amyotrophic lateral sclerosis according to the invention. Nevertheless, the preferred compounds of formula I are those corresponding to the formulae

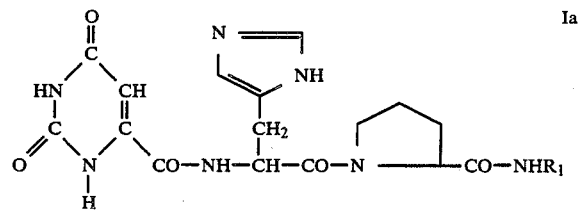

and

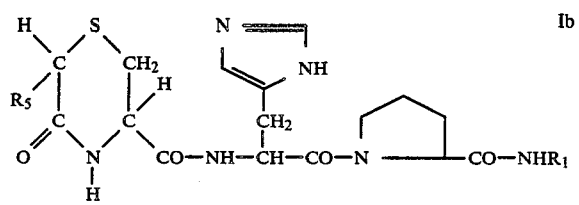

wherein $R_1$ and $R_5$ have the same meaning as above.

Preferably in formulas I, Ia and Ib, respectively, $R_1$ represents a hydrogen atom.

Especially preferred members of the compounds of formula I are orotyl-L-histidyl-L-prolinamide and 5-oxo-6-methyl-thiomorpholine-3(L)carbonyl-L-histidyl-L-prolinamide, or their hydrates or pharmaceutically acceptable salts.

The manner in which the compound of formula I is administered to a patient suffering from amyotrophic lateral sclerosis, i.e. the application form and place (on the patient's body), in principle depends on the state of disease in the individual patient to be treated. In general it is preferred to start the medication with preparations containing the active ingredient of formula I which are suitable for infusions, especially intrathecal infusions, or for intravenous, intramuscular or intraperitoneal injections. Such preparations are known per se and normally consist of a bottle closed with a rubber stopper and containing the desired amount of the active compounds in sterile, dry (lyophilized) form. By adding a suitable physiologically acceptable solvent such as, for example, sterile isotonic aqueous solutions of sodium chloride, glucose, inositol or the like, in which the compounds of formula I are readily soluble, and adjusting the resulting solution (which may be used as it is for injections) to the appropriate volume by adding it to a desired amount of the same solvent in an infusion flask, a solution useful for administration by infusion is obtained.

Spray forms are very useful application forms for intranasal or oral applications of the compounds of formula I or for the administration of these substances to the bronchia. Such sprays can be prepared by techniques known in the art.

Oral application forms of the compounds of formula I are especially useful to maintain the improvements in the state of disease resulting from an introductory treatment with infusions or injections. Such oral application forms like tablets, dragees, capsules, granules, drops and syrups are known per se. In their production generally used inorganic or organic adjuvants such as diluents, carriers, binders, lubricants, colors, flavorings, etc. are added to the compounds of formula I.

For instance tablets or dragees, each containing 20 mg of a compound of formula I, may be prepared by mixing 20 g of the respective ingredient of formula I together with 35 g of corn starch, 10 g of colloidal silica, 5 g of magnesium stearate and, if desired, colors and/or flavorings. The blend is granulated, dried and compressed into 1000 tablets which may subsequently be film-coated or sugar-coated.

Capsules, each containing 20 mg of the compound of formula I, may be prepared, for instance, by mixing 20 g of the active ingredient with 376 g of lactose, granulating the mixture with an aqueous solution of 4 g gelatine, drying and finally filling into 1000 hard-shell gelatine capsules.

Drops for intranasal application, which may also be used in the form of a spray, can be obtained in a known manner by dissolving the compound of formula I in an isotonic aqueous solution of sodium chloride, mannitol, sorbitol, inositol or the like and adding an adhesive such as polyvinyl pyrrolidone or polyvinyl alcohol and/or a preservative such as 4-hydroxybenzoic acid methyl ester or benzyl alcohol.

Suppositories containing an active ingredient of formula I may be prepared by melting 95 g of a commercially available suppositories base at about 40° to 45° C., adding 3 g of a salicylic or mandelic acid, followed by adding, while stirring, 2 g of the active ingredient and pouring the mixture into molds.

In many cases compositions for percutaneous application of the compounds of formula I, such as plasters or the like, containing a solution of the active ingredient are also very convenient. Such compositions may optionally also contain a known membrane penetration enhancer such as an N-alkyl lactam, etc.

The pharmaceutical compositions mentioned above for oral, rectal, percutaneous or intramuscular administration of the compounds of formula I desirably may be the type from which the active ingredient has a delayed release. Thus for a longer period of time, for instance 24 hours, a steady supply of the active ingredient to the ALS patient can be attained.

The amounts of the compounds of formula I to be administered to the ALS patients depend—besides their application form and place—on the state of the disease in the individual patient at the onset of treatment and are to be determined individually by the physician. In general it is advisable to initially administer about 0.01 to 0.25 millimoles per day by infusion.

The surprising activity of the compounds of formula I and of medicaments containing these ingredients in the treatment of ALS patients can be seen from the following examples of effects which resulted after administration of orotyl-L-histidyl-L-prolinamide in clinical studies. This active ingredient was filled in lyophilized form in 6 mg portions in bottles, closed with rubber stoppers, also containing 12 mg mannitol.

EXAMPLE 1

A patient with bulbar palsy caused by ALS was treated three times daily (at 4 hour intervals) on four consecutive days in form of short infusions (i.e. within 30 minutes) with the active ingredient. The total cumulative doses were on the first day 18 mg, on the second day 36 mg, on the third day 54 mg and on the fourth day 72 mg. The single doses for each infusion were dissolved in 100 ml of a sterile isotonic solution of sodium chloride. As a result of the treatment, remarkable improvements in the bulbar symptoms could be observed, and, for instance, the patient became able to speak. The side effects of this treatment were insignificant and could be neglected in consideration of the improvement obtained which remained for several days after the medication had ended.

EXAMPLE 2

Another ALS patient, suffering for eight months from ALS, was treated in the same manner as described above. He showed striking improvement in muscle weakness. For instance, he became able to lift his arms above horizontal, to walk without a stick, to climb stairs without support, and he became independent in activities of everyday life (such as shaving, washing, cutting with a knife, using a fork, writing, etc.). When the four days therapy was finished this improvement was sustained for some days, and thereafter it declined during the course of the following weeks.

EXAMPLE 3

Three other ALS patients, who had been ill for five, seven and twelve months, respectively, were each treated on four consecutive days three times daily with 24 mg of the active ingredient, dissolved in 5% aqueous glucose solution, by intravenous infusion, applied within 30 minutes. Remarkable improvements were noted in using buttons and zippers and in the ability to walk without assistance. Clonic reflexes changed to normal, and the tendency to become fatigued was reduced in these patients. Again the observed side effects were insignificant and could be neglected.

EXAMPLE 4

In one ALS patient having a pronounced atrophy of the muscles of the hands, application of a total of only 18 mg of the active compound on one day (infusion of 6 mg each time at intervals of four hours) caused an evident effect on the hand musculature which after ending of the medication remained for some time.

Similar results have also been observed in ALS patients upon administration of orotyl-L-histidyl-L-prolinamide in other pharmaceutical application forms as well as on administration of further compounds of formula I in appropriate pharmaceutical compositions, especially in medicaments for application by infusion or injection.

The foregoing description and examples have been set forth merely to illustrate and exemplify the invention and are not intended to limit its scope. Since modifications of the described embodiments incorporating the spirit and substance of the invention may occur to persons skilled in the art, the scope of the invention should be limited solely with respect to the appended claims and equivalents.

What is claimed is:

1. A method of treating patients suffering from amyotrophic lateral sclerosis to obtain improvement in the clinical symptoms thereof comprising administering an effective amyotropic lateral sclerosis symptom counteracting amount of a dipeptide derivative corresponding to the formula

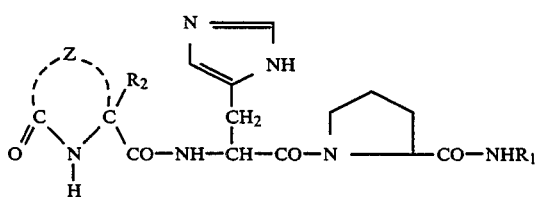

wherein
$R_1$ represents a hydrogen atom, an alkyl group containing one to six carbon atoms, a cyclohexyl group or a benzyl group,
Z is one of the following groups (attached to the CO-group in the ring by the valence marked with an asterisk)

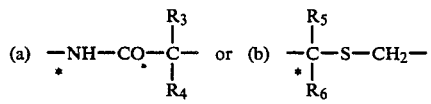

wherein if Z represents a group (a), $R_2$ and $R_3$ together represent an additional bond between the carbon atoms to which $R_2$ and $R_3$ are attached, or if Z represents a group (b), $R_2$ is a hydrogen atom,
$R_4$ and $R_5$ may be the same or different and each represent hydrogen or an alkyl group containing one to three carbon atoms, or $R_5$ also may represent a phenyl group, and
$R_6$ represents a hydrogen or a methyl group, in anhydrous or hydrated form, or a pharmaceutically acceptable salt of such a compound with an acid.

2. The method of claim 1 wherein the dipeptide derivative corresponds to the formula

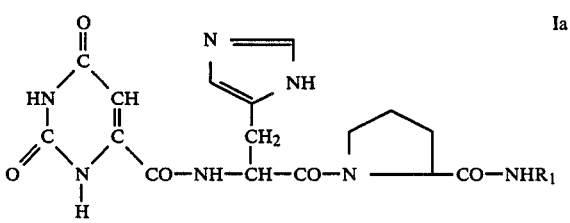

wherein $R_1$ is as defined in claim 1.

3. The method of claim 1 wherein the dipeptide derivative corresponds to the formula

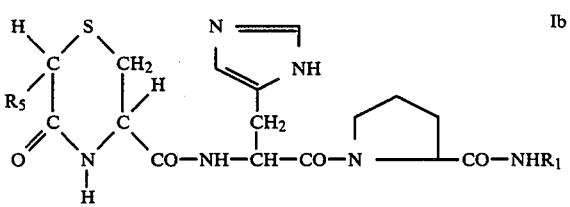

wherein $R_1$ and $R_5$ are as defined in claim 1.

4. The method of claim 1 wherein $R_1$ represents a hydrogen atom.

5. The method of claim 2, wherein the dipeptide derivative of formula Ia is orotyl-L-histidyl-L-prolinamide.

6. The method of claim 3, wherein the dipeptide derivative of formula Ib is 5-oxo-6-methyl-thiomorpholine-3-(L)-carbonyl-L-histidyl-L-prolinamide.

7. The method of claim 1, wherein the administration of the compound of formula I is parenteral or percutaneous.

8. The method of claim 7 wherein the administration is by infusion.

9. The method of claim 1, wherein the administration of the compound of formula I is oral or rectal.

10. The method of claim 1, which comprises administering repeated, periodic doses of the compound of formula I.

* * * * *